United States Patent
Jacobson et al.

(10) Patent No.: US 6,487,915 B1
(45) Date of Patent: Dec. 3, 2002

(54) METHOD FOR CHARACTERIZING RESIDUAL STRESS IN METALS

(75) Inventors: Loren A. Jacobson, Santa Fe, NM (US); David J. Michel, Alexandria, VA (US); Jeffrey R. Wyatt, Burke, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/964,549

(22) Filed: Sep. 28, 2001

(51) Int. Cl.$^7$ ................................................ G01N 29/00
(52) U.S. Cl. ........................... 73/801; 73/587; 73/590
(58) Field of Search ............................. 73/801, 78, 81, 73/85, 587, 590

(56) References Cited

U.S. PATENT DOCUMENTS

| | | | |
|---|---|---|---|
| 3,946,600 A | * | 3/1976 | Rettig et al. .................. 73/71.4 |
| 4,033,182 A | | 7/1977 | Clotfelter |
| 4,249,423 A | * | 2/1981 | Viertl et al. .................. 73/783 |
| 5,166,613 A | | 11/1992 | Perry |
| 5,723,792 A | | 3/1998 | Miyazaki |

FOREIGN PATENT DOCUMENTS

| | | |
|---|---|---|
| JP | 59218934 | 12/1984 |
| JP | 59221657 | 12/1984 |
| JP | 61254849 | 11/1986 |
| JP | 62365134 | 7/1987 |

* cited by examiner

Primary Examiner—Harshad Patel
Assistant Examiner—Corey D. Mack
(74) Attorney, Agent, or Firm—John J. Karasek; George A. Kap

(57) ABSTRACT

A method is provided for measuring the residual stress in metals. The method includes the steps of drilling one or more holes in a metal workpiece to a preselected depth and mounting one or more acoustic sensors on the metal workpiece and connecting the sensors to an electronic detecting and recording device. A liquid metal capable of penetrating into the metal workpiece placed at the bottom of the hole or holes. A recording is made over a period of time (typically within about two hours) of the magnitude and number of noise events which occur as the liquid metal penetrates into the metal workpiece. The magnitude and number of noise events are then correlated to the internal stress in the region of the workpiece at the bottom of the hole.

7 Claims, 1 Drawing Sheet

METHOD FOR CHARACTERIZING RESIDUAL STRESS IN METALS

FIELD OF THE INVENTION

The present invention relates to measuring or testing methods for measuring residual stress in metals.

BACKGROUND OF THE INVENTION

In general, there are three basic methods for measuring residual stress in metals. A relatively primitive method involves simply making careful measurements of the dimensions of a metal sample and observing any changes in the dimensions of the metal material as the sample is being machined. It will be appreciated that this approach is tedious and requires removal of significant portions of the metal material in carrying out the method.

A second method involves the use of neutron diffraction. An important disadvantage of this method is that it requires a source of neutrons and other expensive apparatus.

A third method involves x-ray diffraction. One limitation of this method is that x-ray diffraction is limited to the surfaces of metal samples because of the low penetrability of x-rays.

Patented prior art of general interest includes the following U.S. Pat. Nos. 5,723,792 (Miyazaki); 5,166,613 (Perry); and 4,033,182 (Clotfelter) and the following Japanese patents: JP 62165134 (Yasua); JP 61254849 (Tayaki); JP 59221657 (Hideo); and JP 59218934 (Akihiko). Briefly considering these references, the Miyazaki patent discloses a stress measuring device wherein a hole is formed in the stress concentration region of a structure in which the stress is to be measured and a plurality of different stress sensors are selectively installed in the hole. The Perry patent discloses a method and device for mapping stress within ferromagnetic materials by analyzing Barkhausen noise generated by introducing magnetic fields. The Clotfelter patent discloses a method of measuring stress in test articles by obtaining a series of transit time differentials between a second wave echo for a longitudinal wave and a first wave echo for each of a pair of shear waves propagated through the specimen. The Yasuo patent discloses a method for measuring stress in steel frames by injecting a pressurized liquid such as water into a cavity in the frame. The Toyoki patent discloses a nondestructive method for measuring stress produced on the surface of an object by measuring the relation between the acoustic velocity changing ratio and stress value of the material of the object, and the velocity of the surface wave sound of the object to be measured. The Hideo patent discloses a method for determining whether a ceramic product is defective by measuring acoustic emissions from the product. The Akihiko patent discloses a method for testing the strength of ceramics by measuring stress during a sound production caused by extremely small rupturing of the ceramic to be tested.

SUMMARY OF THE INVENTION

In accordance with the invention, a method is provided for characterizing residual stress in metals which is simple and quick, which provides a limited amount of damage or disturbance to the workpiece or sample under test and which has an essentially unlimited depth capacity.

In accordance with the invention, a method is provided for measuring the residual stress in metals, the method comprising the steps of: (a) drilling at least one hole in a metal workpiece to a pre-selected depth; (b) mounting one or more acoustic sensors on the metal workpiece and connecting the sensor or sensors to an electronic detecting and recording device; (c) placing at the bottom of the hole a liquid metal capable of penetrating into the metal workpiece; (d) recording over a period of time the magnitude and number of noise events which occur as the liquid metal penetrates into the metal workpiece; and (e) correlating the magnitude and number of noise events recorded to the internal stress in the region of the workpiece at the bottom of the hole.

Advantageously, the acoustic sensor comprises at least one microphone.

In one preferred embodiment, the metal comprises an aluminum workpiece and the liquid metal is selected from the group consisting of gallium and a gallium-containing alloy. In another embodiment, the metal workpiece comprises a steel workpiece and hydrogen is used to probe the workpiece.

Preferably, the period of time is within about two hours.

In an advantageous implementation, the drilling step comprises drilling a plurality of holes into said workpiece, and a plurality of microphones are used for simultaneously testing said plurality of holes by correlating each detected noise event with the hole at which the noise event originated.

In a further embodiment, the liquid metal comprises a liquifiable metal capable of melting at a predetermined temperature and the temperature of the metal workpiece is raised to at least said predetermined temperature so as to produce melting of the liquifiable metal.

Further features and advantages of the present invention will be set forth in or apparent from, the detailed description of preferred embodiments thereof which follows.

DESCRIPTION OF THE PREFERRED EMBODIMENTS

Figure 1:
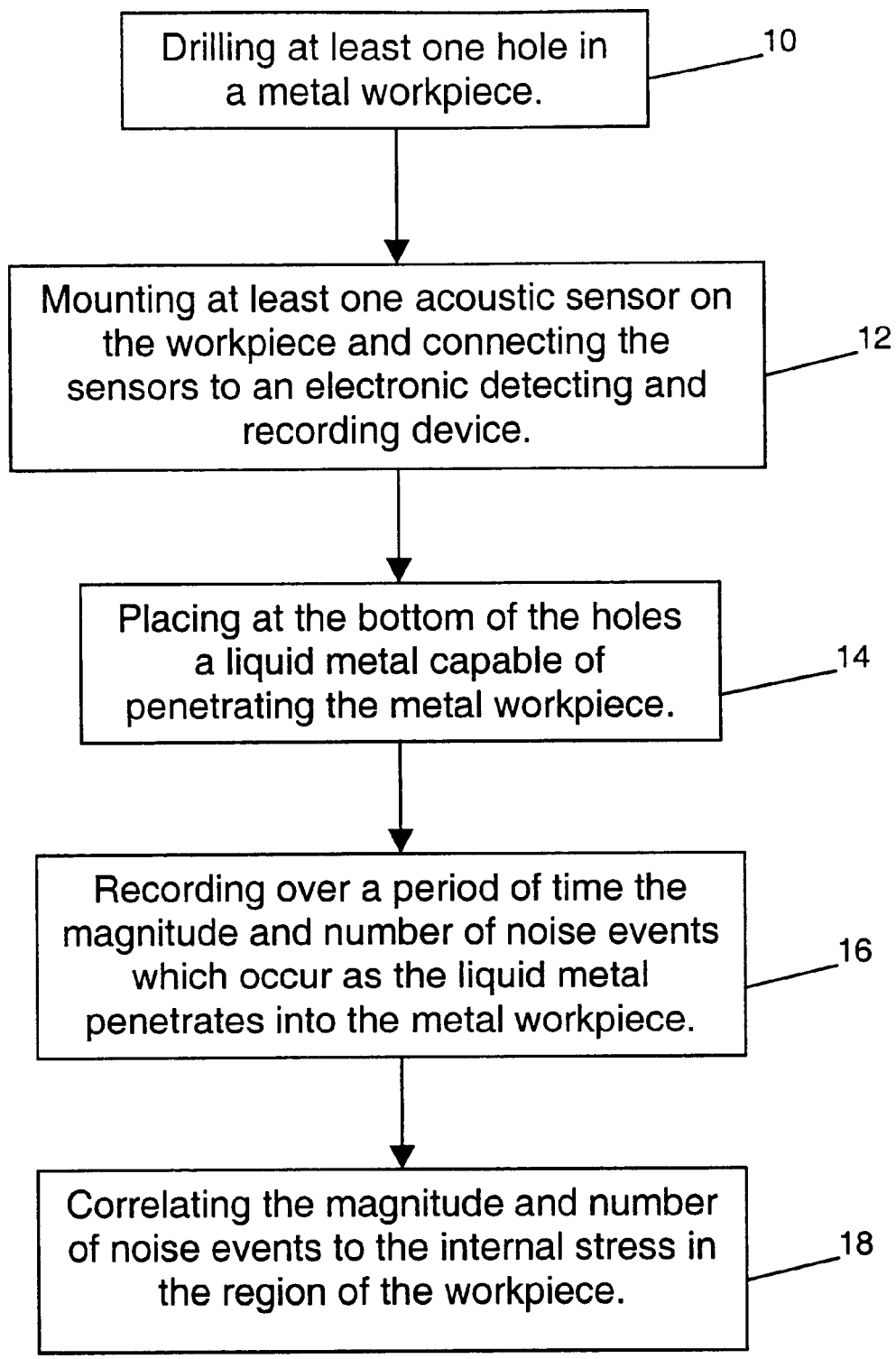
FIG. 1 is a block diagram of a preferred embodiment of the method of the invention.

As indicated above, the method of the invention involves a series of steps which yield a quick result with a limited amount of disturbance of the sample. As a first step, indicted by block 10, the metal sample under test has at least one hole drilled therein to the depth desired for testing. The hole diameter is typically 5 mm although the hole diameter is not critical and other hole diameters can be used. Plural holes can be drilled in the sample if desired, as is discussed in more detail below.

In the next step, indicated by block 12, at least one acoustic sensor, e.g., a microphone, is mounted on the sample and connected to a conventional electronics unit for producing output corresponding to the acoustic signals (e.g., noise events) detected by acoustic sensor. Microphones and associated electronics of this type are typically used in measurements of acoustic emissions in connection with probing occurrences or cracking in samples. Suitable microphones and electronics are those sold commercially by Physical Acoustics Corporation.

In the next step, indicated by block 14, a liquid metal is injected into or otherwise placed in the drilled hole at the bottom thereof. In a specific example, a 100 mg of the liquid metal is used. A range of about 10 mg to about 100 mg is desirable. Different liquid materials can be used and where, for example, the metal sample is aluminum, gallium and gallium containing alloys are suitable. In general, the liquid metal or alloy is chosen so as to cause noise at room temperature, although for initial materials for which there are no liquid metals or alloys that cause noise at room temperature, the testing can be performed at elevated temperatures with suitable low All melting point materials. Hydrogen is a potential candidate for use as a stress probe for steels.

As indicated by block 16, as the liquid metal penetrates the sample, the magnitude and number of noise events is detected and recorded by the microphone and associated electronics. This detecting and recording step is carried out over an extended period of time. In a typical example, this time period is within about two hours, a minimum period of time being about 20 minutes.

After recordation, as indicated by block 18, the noise events are correlated to the internal stress in the region at the bottom of the drilled hole.

In another embodiment, two or more microphones are used in order to permit the position of the noise event to be determined. This approach is of particular advantage in simultaneously testing a relatively large number of drilled holes.

Although the invention has been described above in relation to preferred embodiments thereof, it will be understood by those skilled in the art that variations and modifications can be effected in these preferred embodiments without departing from the scope and spirit of the invention.

What is claimed is:

1. A method for measuring the residual stress in metals, said method comprising the steps of:
   (a) drilling at least one hole in a metal workpiece to a pre-selected depth;
   (b) mounting at least one acoustic sensor on the metal workpiece and connecting the at least one acoustic sensor to an electronic detecting and recording device;
   (c) placing at the bottom of the hole a liquid metal capable of penetrating into the metal workpiece that causes noise;
   (d) recording over a period of time the magnitude and number of noise events which occur as the liquid metal penetrates into the metal workpiece; and
   (e) correlating the magnitude and number of noise events recorded to the internal stress in the region of the workpiece at the bottom of the hole.

2. The method according to claim 1, wherein said acoustic sensor comprises at least one microphone.

3. The method according to claim 1, wherein the metal workpiece comprises an aluminum workpiece and wherein the liquid metal is selected from the group consisting of gallium and a gallium-containing alloy.

4. The method according to claim 1, wherein the metal workpiece comprises a steel workpiece and wherein liquid metal is used to probe the workpiece.

5. The method according to claim 1, wherein said period of time is between of from about twenty minutes to about two hours.

6. The method according to claim 1, wherein said drilling step comprises drilling a plurality of holes into said workpiece, and wherein a plurality of microphones are used for simultaneously testing said plurality of holes by correlating each detected noise event with the hole at which the noise event originated.

7. The method according to claim 1, wherein the liquid metal comprises a liquifiable metal capable of melting at a predetermined temperature and the temperature of the metal workpiece is raised to at least said predetermined temperature so as to produce melting of said liquifiable metal.

* * * * *